United States Patent

Hajima et al.

[11] Patent Number: 6,018,049
[45] Date of Patent: Jan. 25, 2000

[54] PROCESS FOR THE PREPARATION OF CARBAMOYLATED IMIDAZOLE DERIVATIVES

[75] Inventors: Makoto Hajima, Hirakata; Yoshiyuki Takeuchi, Kawanishi; Koji Matsuda, Takatsuki, all of Japan

[73] Assignee: Shionogi & Co., Ltd., Japan

[21] Appl. No.: 09/319,704

[22] PCT Filed: Dec. 19, 1997

[86] PCT No.: PCT/JP97/04706

§ 371 Date: Jun. 10, 1999

§ 102(e) Date: Jun. 10, 1999

[87] PCT Pub. No.: WO98/29394

PCT Pub. Date: Jul. 9, 1998

[30] Foreign Application Priority Data

Dec. 26, 1996 [JP] Japan ................................ 8-347508

[51] Int. Cl.[7] ...................... C07D 233/84; C07D 401/06
[52] U.S. Cl. ....................... 546/274.4; 548/324.1
[58] Field of Search ................. 546/274.4; 548/324.1

[56] References Cited

U.S. PATENT DOCUMENTS 5,910,506  6/1999  Sugimoto et al. ...................... 514/397

FOREIGN PATENT DOCUMENTS

WO 96/10019  4/1996  WIPO .

OTHER PUBLICATIONS

CA 120: 271118p 5–Nitroimidazoles . . . thiols. Girard et al., p. 1148, 1994.

Primary Examiner—Joseph K. McKane
Attorney, Agent, or Firm—Wenderoth, Lind & Ponack, L.L.P.

[57] ABSTRACT

The present invention provides a process for the preparation of a compound of the formula (III):

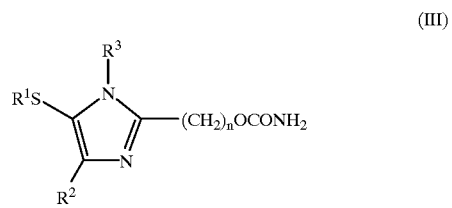

(III)

wherein $R^1$ is an optionally substituted alkyl or an optionally substituted aryl; $R^2$ is an optionally substituted alkyl: $R^3$ is an optionally substituted alkyl, an optionally substituted alkenyl, an optionally substituted aralkyl, or an optionally substituted heteroarylalkyl; and n is an integer of 1–3, which comprises reacting a compound of the formula (I):

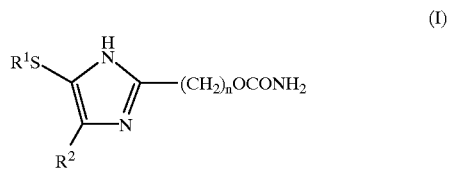

(I)

wherein $R^1$, $R^2$, and n are as defined above, with a compound of the formula (II):

$R^3OH$ (II)

wherein $R^3$ is as defined above, in the presence of phosphine and either of dialkyl azodicarboxylate and tetraalkyl azodicarboxamide.

8 Claims, No Drawings

PROCESS FOR THE PREPARATION OF CARBAMOYLATED IMIDAZOLE DERIVATIVES

This application is a 371 of PCT/JP97/04706 filed Dec. 19, 1997.

TECHNICAL FIELD

The present invention relates to a process for the preparation of carbamoylated imidazole derivatives.

BACKGROUND ART

Various imidazole derivatives have been researched to apply them to medicines, and they are assumed to be efficient as an antiviral agent or an anti-HIV agent.

It is described, as a process for the preparation of imidazole derivatives, that alcohol derivatives are reacted with 4,5-dicyanoimidazole, diethylazodicarboxylate, and triphenylphosphine (Tetrahedron Asymmetry. Vol. 5, No. 2, 181–184 (1994)). This process does not, however, include N-alkylation reaction of carbamoylated imidazole derivatives. It is described, as a process for the preparation of imidazole derivatives having a carbamoyl group at 2-position, that introduction of a carbamoyl group into 2-position of the imidazole ring is carried out after alkylation at 1-position (WO 96/10019). The reaction condition of the alkylation in this method is not mild.

DISCLOSURE OF INVENTION

The present inventors have intensively studied to develop, as a process for the preparation of carbamoylated imidazole derivatives, N-alkylation under mild condition without protection of the carbamoyl group, and succeeded in the reaction of imidazole derivatives of the following formula (I) with the compounds of the formula (II) in the presence of phosphine and either of dialkyl azodicarboxylate and tetraalkyl azodicarboxamide to give imidazole derivatives of the formula (III). Thus, the present invention has been accomplished.

Accordingly the present invention provides a process for the preparation of a compound of the formula (III):

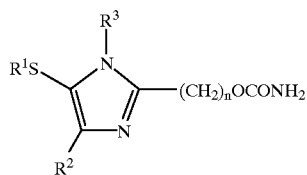

(III)

wherein $R^1$ is an optionally substituted alkyl or an optionally substituted aryl; $R^2$ is an optionally substituted alkyl; $R^3$ is an optionally substituted alkyl, an optionally substituted alkenyl, an optionally substituted aralkyl, or an optionally substituted heteroarylalkyl; and n is an integer of 1–3, which comprises reacting a compound of the formula (I):

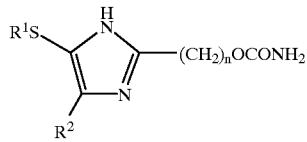

(I)

wherein $R^1$, $R^2$, and n are as defined above, with a compound of the formula (II):

$$R^3OH \qquad (II)$$

wherein $R^3$ is as defined above, in the presence of phosphine and either of dialkyl azodicarboxylate and tetraalkyl azodicarboxamide.

BEST MODE FOR CARRYING OUT THE INVENTION

Preferable embodiments of the present invention include the process wherein $R^3OH$ is picolyl alcohol, the process wherein dialkyl azodicarboxylate is diisopropyl azodicarboxylate, and/or the process wherein phosphine is triphenylphosphine.

In the present specification, the term "alkyl" means a C1–C8 straight or branched chain alkyl, for example, methyl, ethyl, n-propyl, i-propyl, n-butyl, i-butyl, t-butyl. n-pentyl, i-pentyl, n-hexyl, n-heptyl, n-octyl, and the like. The alkyl may be substituted with halogen (fluoro, chloro, bromo, or iodo), aryl, cycloalkyl (e.g., cyclopropyl), and the like. One or more substituent(s) may be at any substitutable position(s).

The term "aryl" means a C6–C12 aromatic group, for example, phenyl, naphthyl, and the like. The aryl may be substitute with halogen, alkyl (e.g., methyl or ethyl), alkoxy (e.g., methoxy or ethoxy), nitro, and the like. One or more substituent(s) may be at any substitutable position(s). Examples of a substituted aryl include, for example, 3-fluorophenyl, 3-chlorophenyl, 3,5-difluorophenyl, 3,5-dichlorophenyl, 3-methylphenyl, 3,5-dimethylphenyl, 3-methoxyphenyl, 3,5-dimethoxyphenyl, 3-nitrophenyl, and the like.

The term "alkenyl" means a C2–C8 straight or branched alkenyl, for example, vinyl, allyl, propenyl, butenyl, pentenyl, hexenyl, heptenyl, and the like. The substituent on the alkenyl is the same as that on the above defined alkyl.

The term "aralkyl" means the above defined alkyl substituted with the above defined aryl, for example, benzyl, 1-phenylethyl, naphthylmethyl, 2-naphthylethyl, and the like. The substituent on the aralkyl is the same as that on the above defined aryl.

The term "heteroarylalkyl" means the above defined alkyl substituted with heteroaryl. The heteroaryl means a 5–6 membered cyclic group which contains one or more hetero atoms selected independently from the group consisting of oxygen, sulfur, and nitrogen atoms in the ring, and is optionally condensed with a carbon ring or other heterocyclic group at any substitutable position(s), for example, pyridlyl (e.g., 4-pyridyl), pyridazinyl (e.g., 5-pyridazinyl), pyrimidinyl (e.g., 4-pyrimidinyl), pyrazinyl (e.g., 2-pyrazinyl), imidazolyl (e.g., 2-imidazolyl), oxazolyl (e.g., 4-oxazolyl), thiazolyl (e.g., 5-thiazolyl), thienyl (e.g., 2-thienyl), quinolyl (e.g., 2-quinolyl), and the like. The heteroarylalkyl includes pyridylmethyl (e.g., 4-pyridylmethyl), pyridylethyl (e.g., 1-(2-pyridyl)ethyl), pyridazinylmethyl (e.g., 5-pyridazinylmethyl), pyrimidinylmethyl (e.g., 4-pyrimidinylmethyl), pyrazinylmethyl (e.g., 2-pyrazinylmethyl), imidazolylmethyl (e.g., 1-methyl-2-imidazolylmethyl), oxazolylmethyl (e.g., 4-oxazolylmethyl), thiazolylmethyl (e.g., 5-thiazolylmethyl), thienylmethyl (e.g., 2-thienylmethyl), quinolylmethyl (e.g., 2-quinolylmethyl), and the like. The substituent on the heteroaryl is the same as that on the above defined aryl.

The present invention provides a process for the preparation of the imidazole derivative of the formula (III), which comprises reacting the compound of the formula (I) with the compound of the formula (II) in the presence of phosphine and either of dialkyl azodicarboxylate and tetraalkyl azodicarboxamide. The compound of the formula (I), a starting material of the present invention, includes known ones and may be produced according to the method described in the International Patent Publication WO 96/10019. The compound of the formula (I) to be used in the present invention is, for example, 5-(3,5-dichlorophenyl)thio-4-isopropyl-1H-imidazol-2-ylmethyl carbamate, 5-n-butylthio-4-ethyl-1H-imidazol-2-isopropyl carbamate, 5-(4-nitrophenylthio)-4-(2-ethylpropyl)-1H-imidazol-2-ylethyl carbamate, 5-(2,3,4-trichlorophenylthio)-4-isopropyl-1H-imidazol-2-ylmethyl carbamate, and the like.

The compound (II) includes picolyl alcohol (e.g., γ-picolyl alcohol), ethanol, cyclohexylmethyl alcohol, chloro ethanol (e.g., 1-chloro ethanol), ethyl glycolate, 2-hydroxyacetophenone, allyl alcohol, 4-methylbenzylalcohol, furfuryl alcohol, carbamoyloxy ethanol, and the like.

Dialkyl azodicarboxylate to be used for the reaction of the compound (I) with the compound (II) is, for example, diisopropyl azodicarboxylate, diethyl azodicarboxylate, and the like. Tetraalkyl azodicarboxamide is, for example, tetramethyl azodicarboxamide, and the like. Phosphine is, for example, triarylphosphine (e.g., triphenylphosphine, tri-o-tolylphosphine, tri-m-tolylphosphine, tri-p-tolylphosphine), trialkylphosphine (e.g., trimethylphosphine, triethylphosphine, tri-n-propylphosphine, triisopropylphosphine, tri-n-butylphosphine, tri-t-butylphosphine), and the like. A solvent is, for example, an aprotic solvent (e.g., tetrahydrofuran, dichloromethane, toluene, ethyl acetate, acetonitrile).

In the reaction of the present invention, the amount of dialkyl azodicarboxylate or tetraalkyl azodicarboxamide is 1.0–2.0 mole equivalents, preferably 1.5–1.7 mole equivalents to the compound (I), the amount of phosphine is 1.0–2.0 mole equivalents, preferably 1.5–1.7 mole equivalents to the compound (I), and the amount of the compound (II) is 1.0–1.5 mole equivalents, preferably 1.1–1.2 mole equivalents to the compound (I). The reaction temperature can be 5–30° C., preferably 15–20° C.

The following examples are provided to further illustrate the present invention and are not to be construed as limiting the scope thereof.

The meanings of the following abbreviations in the examples are shown below.

Bn benzyl

REFERENCE EXAMPLE 1

5-(3,5-Dichlorophenyl)thio-4-isopropyl-1H-imidazol-2-ylmethyl carbamate 3

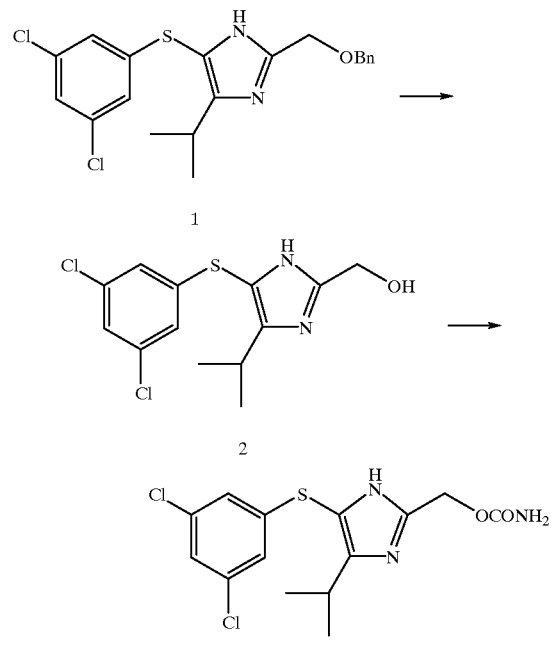

(Step 1)

[5-(3,5-Dichlorophenyl)thio-4-isopropyl-1H-imidazol-2-yl]methanol 2

To the compound 1 10.0 g (24.5 mmol) was added aqueous concentrated hydrochloric acid 50 ml. The mixture was stirred at 80° C. for 5 hours. To the reaction mixture were added water 50 ml and toluene 30 ml. The toluene layer was removed and the aqueous layer was neutralized by dropwising 30% aqueous sodium hydroxide. To the mixture was added ethyl acetate 80 ml and the objective was extracted. The ethyl acetate layer was separated and washed with water 30 ml. Each aqueous layer was extracted with ethyl acetate 30 ml, and which was combined with the above obtained ethyl acetate layer. The ethyl acetate solution was concentrated under reduced pressure. The obtained slurry was stirred under ice cooling for 2 hours, filtered, washed with cooled ethyl acetate, and dried to yield the compound 2 6.8 g as a white crystal. Yield 87%.

mp 191–192° C.

$^1$H-NMR (d$_6$-DMSO-TMS) δ ppm; 1.17 (d, J=7.0 Hz, 6H), 3.0–3.2 (m, 1H), 4.47 (d, J=5.0 Hz, 2H), 5.47 (t, J=5.0 Hz, 1H), 6.99 (s, 2H), 7.31 (s, 1H), 12.4 (bs, 1H).

(Step 2)

5-(3,5-Dichlorophenyl)thio-4-isopropyl-1H-imidazol-2-ylmethyl carbamate 3

The compound 2 40 g (126 mmol) obtained in the step 1 was suspended in acetonitrile 400 ml, and the suspension was cooled down under nitrogen atmosphere. To the suspension was added dropwise chlorosulfonyl isocyanate 24.3 g (171 mmol) at −20 to −25° C. for 1 hour. To the mixture was added water 400 ml under 10° C. To the mixture was added concentrated hydrochloric acid 40 ml, and the mixture was stirred at 50° C. for 2 hours. The mixture was cooled down to −10° C. and crystallized at the same temperature for 1 hour. The obtained slurry was filtered, washed with cooled acetonitrile, and dried to yield the compound 3 43.2 g. Yield 83% mp 102–105° C. (dec)

$^1$H-NMR (d$_6$-DMSO-TMS) δ ppm: 1.25 (d, 7Hz, 6H), 3.19 (sept, H1H) 5.17 (br, 2H), 723 (d, J=2Hz, 2H), 7.48 (s, 1H).

Elemental analysis (C$_{14}$H$_{18}$O$_3$N$_3$SCl$_3$) Calcd. (%): C, 40.54; H, 4.37; N, 10.13; S, 7.73; Cl 25.64 Found. (%): C, 39.97; H, 4.36; N, 10.16; S, 7.66; Cl 25.49

EXAMPLE 1

5-(3,5-Dichlorophenyl)thio-4-isopropyl-1-(4-pyridyl)-methyl-1H-imidazol-2-ylmethyl carbamate 4

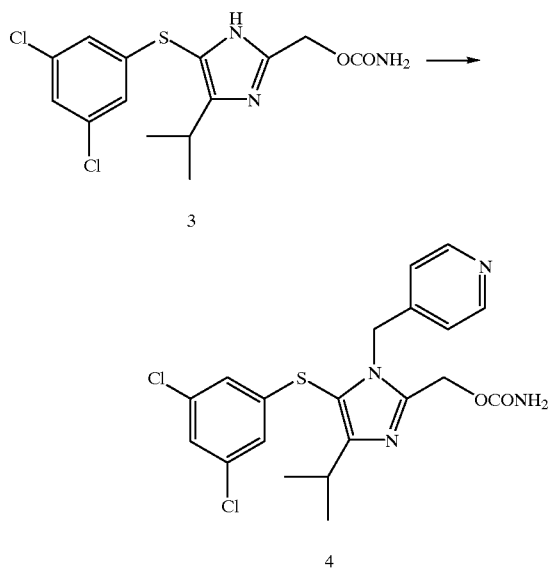

The compound 3 1.0 g (2.41 mmol) obtained in the reference example 1 was suspended in ethyl acetate 10 ml. To the suspension was added 7% aqueous sodium hydrogen carbonate 4 ml, and the ethyl acetate layer was separated. The extract was concentrated under reduced pressure to remove water by using ethyl acetate (10 ml×3) to yield the concentrated solution 10 g. To the concentrated solution were added picolyl alcohol 300 mg (2.75 mmol) and triphenylphosphine 1.0 g (3.97 mmol). To the solution was added dropwise an ethyl acetate solution 7.8 ml of diisopropyl azodicarboxylate 800 mg (3.96 mmol) at 15° C. for 45 minutes. The mixture was stirred for 1 hour at the same temperature. To the reaction mixture was added water 3 ml and 10% hydrochloric acid 2.5 ml with stirring, successively, and the aqueous layer was separated. Further, the ethyl acetate layer was extracted with 3% hydrochloric acid 1.5 ml, and the obtained water layer was combined with the previously obtained aqueous layer. To the aqueous layer was added ethyl acetate 10 ml, and the mixture was neutralized with 7% sodium hydrogen carbonate 14 ml. The ethyl acetate layer was separated, and washed with saturated brine 5 ml, and decolorized with activated carbon 50 mg. The activated carbon was filtered off. The filtrate was concentrated, and mixed with methanol 3 ml. To the mixture was added dropwise water 9 ml to yield a slurry. The slurry was stirred under ice cooling for 1 hour, filtered, washed with water, and dried to yield the compound 4 920 mg as a white crystal. Yield 85%.

$^1$H-NMR (d$_6$-DMSO-TMS) δ ppm: 1.18 (d, J=7.0 Hz, 6H), 2.9–3.1 (m, 1H), 5.11 (s, 2H), 5.30 (s, 2H), 6.66 (bs, 2H), 6.75 (d, J=2.0 Hz, 2H), 6.96 (d, J=6.0 Hz, 2H), 7.27 (t, J=2.0 Hz, 1H), 8.34 (d, J=6.0 Hz, 2H).

INDUSTRIAL APPLICABILITY

The present invention provides a process for N-alkylating carbamoylated imidazole derivatives (I) without protection of the carbamoyl group.

We claim:

1. A process for the preparation of a compound of the formula (III):

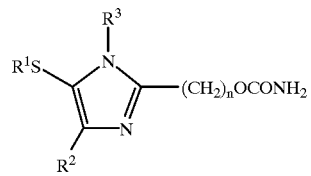

(III)

wherein $R^1$ is an optionally substituted alkyl or an optionally substituted aryl; $R^2$ is an optionally substituted alkyl; $R^3$ is an optionally substituted alkyl, an optionally substituted alkenyl, an optionally substituted aralkyl, or an optionally substituted heteroarylalkyl; and n is an integer of 1–3, which comprises reacting a compound of the formula (I):

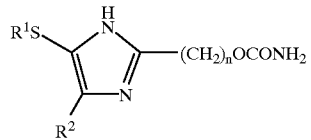

(I)

wherein $R^1$, $R^2$, and n are as defined above, with a compound of the formula (II):

$R^3OH$ (II)

wherein $R^3$ is as defined above, in the presence of phosphine and either of dialkyl azodicarboxylate and tetraalkyl azodicarboxamide.

2. The process as claimed in claim 1 wherein $R_3OH$ is picolyl alcohol.

3. The process as claimed in claim 1 wherein dialkyl azodicarboxylate is diisopropyl azodicarboxylate.

4. The process as claimed in claim 1 wherein phosphine is triphenylphosphine.

5. The process as claimed in claim 2 wherein dialkyl azodicarboxylate is diisopropyl azodicarboxylate.

6. The process as claimed in claim 2 wherein phosphine is triphenylphosphine.

7. The process as claimed in claim 3 wherein phosphine is triphenylphosphine.

8. The process as claimed in claim 5 wherein phosphine is triphenylphosphine.

* * * * *